United States Patent [19]

Raitto

[11] 4,428,384

[45] Jan. 31, 1984

[54] METHOD AND APPARATUS FOR COLLECTING URINE

[75] Inventor: Russell G. Raitto, Fitzwilliam, N.H.

[73] Assignee: Concord Laboratories, Inc., Keene, N.H.

[21] Appl. No.: 354,707

[22] Filed: Mar. 4, 1982

Related U.S. Application Data

[63] Continuation of Ser. No. 70,743, Aug. 29, 1979, abandoned.

[51] Int. Cl.³ .............................................. B01L 3/00
[52] U.S. Cl. .................................................. 128/760
[58] Field of Search .................. 128/743, 203.21, 295, 128/760, 761; 4/144.1, 144.2; 215/200, 211, 224, 316, DIG. 3

[56] References Cited

U.S. PATENT DOCUMENTS

| | | | |
|---|---|---|---|
| 3,021,840 | 2/1962 | Hallamore et al. | 128/203.21 |
| 3,033,222 | 5/1962 | Connolly | 128/760 |
| 3,518,164 | 6/1970 | Andelin et al. | 128/760 |
| 3,777,739 | 12/1973 | Raitto | 128/760 |
| 3,832,738 | 9/1974 | Kliemann | 128/760 |
| 3,878,571 | 4/1975 | Seeley | 4/110 |
| 3,881,465 | 5/1975 | Raitto | 128/760 |
| 3,894,531 | 7/1975 | Saunders, Jr. | 128/743 |
| 3,900,019 | 8/1975 | Logiadis | 128/760 |
| 3,923,040 | 12/1975 | Beach | 128/760 |
| 4,046,138 | 9/1977 | Libman et al. | 128/760 |
| 4,064,760 | 12/1977 | Benjamin | 128/760 |
| 4,244,920 | 1/1981 | Manschott | 128/760 |

Primary Examiner—C. Fred Rosenbaum
Assistant Examiner—T. J. Wallen
Attorney, Agent, or Firm—Sewall P. Bronstein

[57] ABSTRACT

This invention provides a collecting device comprising a container for collection of a specimen, an annular intermediate member removably secured to the open end of the container, a cap protector removably secured to said annular member to close the opening of the annular member and thereby the container, and a cap secured to the cap protector so that the internal surfaces of the cap are protected from contamination. Preferably the annular member, cap protector and cap have identification means and are coded to facilitate recognition and instruction of the user.

14 Claims, 7 Drawing Figures

METHOD AND APPARATUS FOR COLLECTING URINE

This is a continuation, of application Ser. No. 070,743 filed Aug. 29, 1979 now abandoned.

FIELD OF THE INVENTION

This invention relates generally to devices and methods for collecting liquids and, more particularly, to an inexpensive and easy to use device and method for collecting urine specimens while minimizing the chance for contamination thereof during the collection process.

BACKGROUND OF THE INVENTION

The collection of urine specimens for analysis is standard medical procedure and it is desirable that the specimen be obtained for use with substantially little or no contamination which might adversely affect the results of such analysis. Further it is desirable that such devices be capable of easy use by a patient in a clean manner without soiling the patient or the patient's garments.

Many previous collecting devices provide a relatively narrow necked container which, while not too difficult for use by male patients, is more difficult for easy and clean use by female patients. Other devices which attempt to avoid such problems may in some instances be inconvenient or uncomfortable to use or generally appear to be relatively more expensive to manufacture than the device of this invention. Typical examples of such devices are illustrated in U.S. Pat. Nos. 3,923,040; 3,878,571; 3,832,738; 3,900,019; 3,033,222 and the like.

Improved collecting devices having wider necks and affording somewhat easier and more clean use by the patient are illustrated in U.S. Pat. Nos. 4,046,138; 3,881,465; 3,777,739 and the like.

However, most of these collecting devices require the sealing cap to be removed from the bottom of the collecting container, whereby it can be exposed to contamination, as in U.S. Pat. Nos. 3,033,222; 3,518,164; 3,900,019 and 4,046,138; or require the sealing cap to be removed from a sealed bag as in U.S. Pat. Nos. 3,881,465 and 3,777,739; or readily expose the inner surface of the sealing cap to contamination as in U.S. Pat. Nos. 3,878,571 and 3,832,738. Most of such devices remain cumbersome for the patient to use and/or are difficult to instruct the patient in use.

Thus, it can be seen that there remains a need for a collecting device that is easy and inexpensive to manufacture, easy to use by the patient in a clean manner with little or no propensity for contaminating the sample, and for which simple instructions on use can be provided.

SUMMARY OF THE INVENTION

The present invention is a collecting device that fills the above needs for providing a device that is simple and inexpensive to make, simple and easy for the patient to use in a clean manner that reduces or eliminates the risk of contamination of the sample by the patient, and that is easy to instruct the patient in the use thereof.

The collecting device of this invention comprises (1) a container for the collection of a specimen, (2) an annular intermediate member removably secured to the open end of the container, (3) a cap protector removably secured to said annular member to close the opening of the annular member and thereby the container, and (4) a cap removably secured to the cap protector so that the internal surfaces of the cap are protected from contamination. In a preferred embodiment said annular member, said cap protector, and said cap have first, second and third identification means, respectively to facilitate identification of the component for giving instructions.

Preferably said first identification means comprises providing the annular member in a first color, said second identification means comprises providing the cap protector in a second color and said third identification means comprises providing the cap in a third color. The different colors provide easy identification and facilitate recognition of the components for the patient while receiving instructions in the use of the device. The identification means can also comprise numbered tabs on the annular member and cap protector and a numbered or differently colored cap. Most preferably the identification means comprise different colors and numbered parts in combination.

The invention further comprises a method for using the above collecting device to obtain a specimen. The method comprises:

removing the cap protector from the container, said annular member remaining attached to the container and the cap remaining attached to the cap protector to completely protect the cap from contamination;
collecting a specimen in the container;
removing the annular member from the container;
removing said cap protector from said cap; and
sealing the container with said cap The device and method of collecting of this invention provide a minimum of exposure to contamination of the sample while providing an inexpensive, simple and easy to use device for collecting specimens.

DETAILED DESCRIPTION OF THE INVENTION

Figure 1:
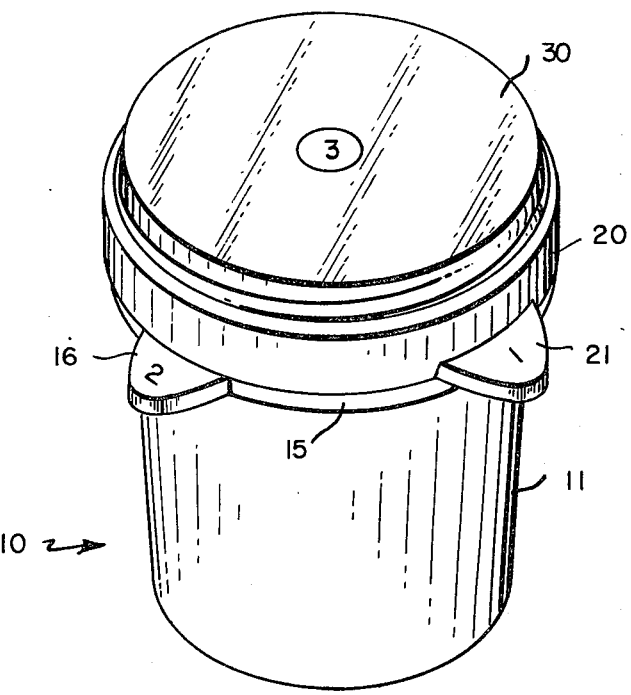
FIG. 1 is a perspective view of a collecting device in accord with the present invention in the form as provided for a patient.
Figure 2:
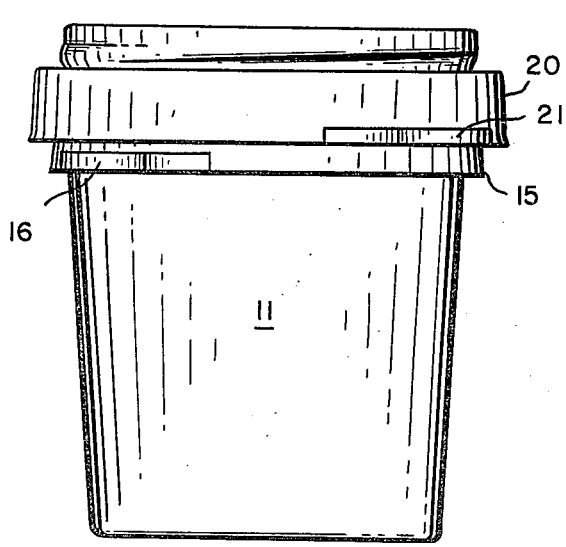
FIG. 2 is a front view of the collecting device of FIG. 1.
Figure 3:
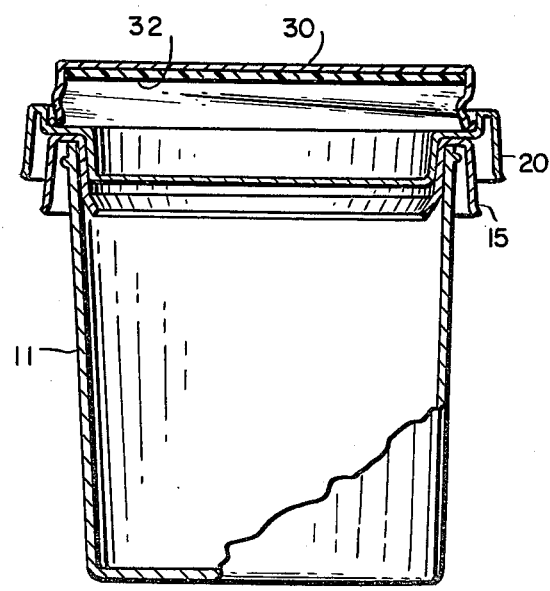
FIG. 3 is a front view, partly in cross-section of the device of FIG. 1.

The invention will now be described in detail with reference to the embodiment illustrated in the accompanying drawings. As can be seen in the drawings, a collecting device 10 in accord with the present invention, as assembled and provided to the patient for use, comprises four major components, a container 11, an annular member 15, a protective cap 20, and a cap 30 for sealing container 11 after use by the patient.

The container 11 has an opening 12 at the top thereof and an externally threaded portion 13 at the open end thereof. The container may be made of any suitable material such as glass or plastic. Preferably the container is made of clear or translucent material and most preferably of a clear plastic.

Annular member 15 is made of suitable plastic material such as, for instance, polystyrene. The annular member 15 has an opening 18 corresponding in size to opening 12 of the container and fits snugly over the open end of the container to keep the top portion of the container clean during use. The annular member is color coded, say yellow, for easy identification of the component. Preferably annular member 15 is provided with a substantially flat tab 16 that can be easily grasped between the fingers of one hand when using the device. Tab 16 can be provided with alpha-numerical identification to further facilitate recognition of the component and use of the device.

Cap protector 20 provides a temporary closure for the container 11 to maintain sterility of the device for collecting the specimen and also provides a protective cover for cap 30 to prevent contamination of the inner surface thereof while the specimen is being collected. Cap protector 20 has bottom portion 24 that fits snugly into the opening 18 of annular member 15 to seal the device until use by the patient. It also is provided with an interior platform 22 and opening 23 that corresponds in size with the rim 35 of cap 30 and cooperate to hold cap 30 snugly in cap protector 20. The protective cap can be made of any suitable plastic material such as, for instance, polystyrene. The cap protector is also color coded, say white, for easy identification of the component. Preferably the cap protector is provided with a substantially flat tab 21 that can be easily grasped between the fingers of one hand when using the device. Tab 21 can be provided with alpha-numerical identification to further facilitate recognition of the component and use of the device.

Cap 30 is internally threaded and has fitted therein a resilient sealing layer 32 made of any suitable compressible material that provides an effective seal when the cap is secured to container 11 after use of the device by the patient. The cap may be made of any suitable material. Conveniently a metal cap is used. The cap is also color coded, say red, for easy identification of the component. The cap can further be provided with alpha-numerical identification to facilitate recognition of the component and use of the device.

The overall device can be neatly assembled for delivery to the user as illustrated in FIG. 1. The assembly can be sterilized and remains sterile until opened by the user.

Figure 4:
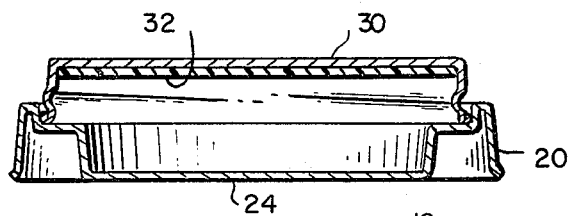
FIG. 4 is a front view, partly in cross-section, of the device of FIG. 1 with the cap protector and cap removed.
Figure 4:
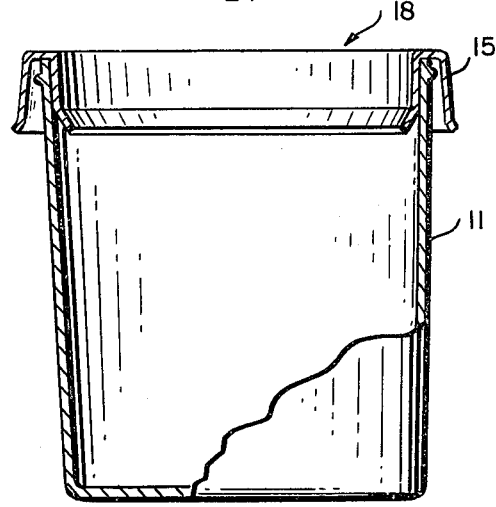
Figure 5:
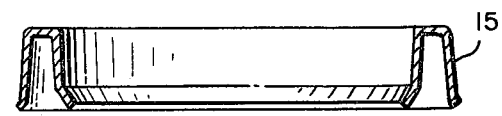
FIG. 5 is a front view, partly in cross-section, of the container of the device of FIG. 1 illustrated with the annular member removed.
Figure 5:
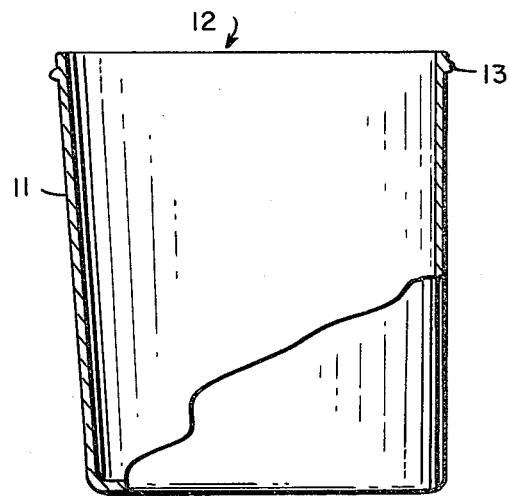
Figure 6:
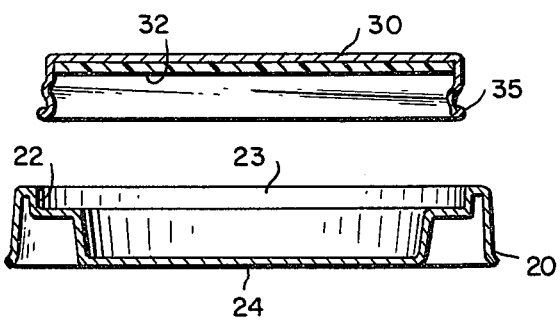
FIG. 6 is a cross-sectional view of the cap and cap protector of the device of FIG. 1 with the cap removed from the cap protector.
Figure 7:
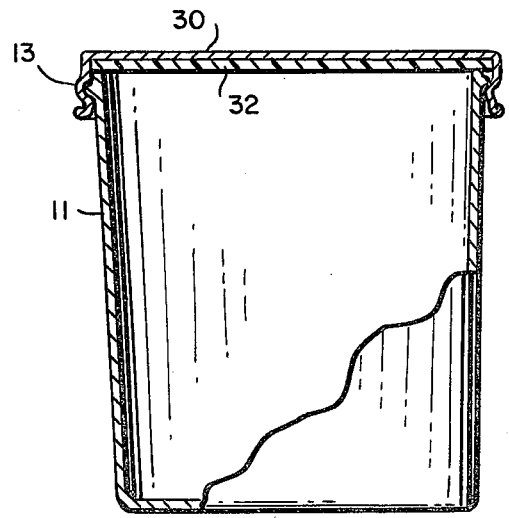
FIG. 7 is front view, partly in cross-section, illustrating the container of the device of FIG. 1 sealed by the cap in a form after use by the patient.

When the device is to be used, the user first removes the cap protector 20 and cap 30 assembly from the container 11 and annular member 15 exposing opening 18. Because the cap 30 remains removably attached to the cap protector 20, it can be placed temporarily on any convenient surface without fear that the inner surface of the cap will become contaminated by contact with anything. When the protected cap is removed, the device is as illustrated in FIG. 4 wherein the annular member 15 effectively covers the upper end and edge of container 11 so that they are not subject to contact with any contaminating surface or with urine during collection of the specimen. Conveniently the container 11 and annular assembly 15 can be held by tab 16 in an appropriate position for voiding into the container via opening 18.

When the voiding process is completed, annular member 15 is removed from container 11 and discarded. Any liquid that inadvertently splashes on annular member 15 is also discarded so that urine that enters the container is not contaminated. The container can be placed on any convenient surface for covering. The diameter of container 11 is conveniently made sufficiently large so that it provides a relatively easy target during use and so that the container is not subject to being easily tipped over when placed on a surface. In a preferred embodiment the container is about 3 inches in height with a diameter of about 2 inches.

To cover container 11, cap 30 is easily removed from the cap protector 20 and threaded onto the container by engaging external thread 13 and tightening until the resilient sealing layer 32 is compressed and effectively seals container 11. Because the specimen that has entered the container has not touched any contaminating surface and because the cap has been fully protected from contamination throughout the process, there is little or no chance for the specimen to become contaminated. Hence, the specimen can be delivered for analysis with the least chance for contamination to have occurred thereto even when the device has been used by the average user who may not normally be too concerned with the necessity for the use of precautionary measures to avoid contamination. The protective components, annular member 15 and cap protector 20, are easily removed and discarded without having to break open seals or tear open bags.

In a preferred embodiment, the disposable components and cap are color coded to provide easy instructions for the use of the device to the average user. Color coding provides for easy recognition of the proper component and ready understanding of the instructions. To further aid in component recognition and understanding of instructions the disposable components and cap can be provided with alpha-numerical characters coordinated with the instructions.

Preferably the assembly of the device 10 as shown in FIG. 1 is internally sterile as provided to the user. Accordingly, the upper edge of container 11 is sterile as well as the upper edge of annular number 15 and internal surface of cap 30 including resilient sealing layer 32. In use the cap protector 20 with cap 30 is aseptically removed from the annular member 15 with container 11, the specimen is collected aseptically in container 11, annular member 15 is aseptically removed from container 11, sterile cap 30 is aseptically removed from cap protector 20 and aseptically secured to container 11 to seal the container. The cap can then be aseptically removed from the container so that the specimen can be aseptically removed from the container for analysis. Accordingly, contamination of the specimen is minimized throughout the entire procedure.

Although the invention has been described in detail, with reference to the preferred embodiments thereof, it will be appreciated that modifications within the spirit and scope of the invention may be effected by the skilled in the art upon reading this disclosure.

I claim:

1. A specimen collecting device comprising a container having an open end formed by a rim for the collection of a specimen, an annular intermediate member removably secured to, over and around the rim of the container to protect the rim against contamination, a cap protector removably secured to and over and around the top portion of said annular member to close the opening of the annular member and thereby the container and to protect the top portion of said intermediate member from contamination, and a cap having a depending annular rim and removably secured within a pocket in said cap protector with the edge portion of said cap rim located in said pocket and with the internal surfaces of the cap facing the internal surfaces of said pocket to form with said pocket a closed chamber whereby said internal surfaces of such cap are protected from contamination both when said cap protector is removed from said intermediate member and when it is secured thereto, said cap being of a size to fit over the container opening and container rim.

2. The specimen collecting device of claim 1 wherein said cap protector has a substantially flat tab that can easily be grasped between the thumb and finger of one hand.

3. The specimen collecting device of claim 2 wherein said annular member comprises a substantially flat tab that can easily be grasped between the thumb and finger of one hand.

4. The specimen collecting device of claim 1 wherein said annular member has first identification means, said cap protector has second identification means and said cap has third identification means for facilitating component recognition by the user.

5. The specimen collecting device of claim 4 wherein said first, second and third identification means comprise color coding of the respective component parts.

6. The specimen collecting device of claim 4 wherein said first, second and third identification means comprise marking the respective component part with one or more alpha-numerical characters.

7. The specimen collecting device of claim 4 wherein said first, second and third identification means comprise both color coding of the respective component part and marking the respective component part with one or more alpha-numerical characters.

8. The specimen collecting device of claim 6 or 7 wherein said annular member and said cap protector are each provided with a substantially flat tab that can easily be grasped between the thumb and finger of one hand and said tab contains one or more alpha-numerical characters thereon.

9. A device according to claim 1, each of said intermediate member and cap protector and cap being color coded to facilitate following use directions to reduce the risk of contamination in use.

10. A device according to claim 9, each of said intermediate member and cap protector having a tab that can be grasped by the fingers of one hand for removal.

11. A specimen collecting device comprising a container having an open end for the collection of a specimen, an annular intermediate member removably secured to the open end of the container, a cap protector removably secured to said annular member to close the opening of the annular member and thereby the container, and a cap removably secured to said cap protector so that the internal surfaces of the cap are protected from contamination both when said cap protector is removed from said intermediate member and when it is secured thereto, said open end of said container being formed by a rim, said intermediate member being channular in cross-sectional shape to form an annular channel in which said rim of said container is removably received and secured, said cap protector having a portion which extends over said opening of said intermediate member to close said opening and then into a depending peripheral annular rim, said portion of said cap protector over said opening having a central recess extending downwardly to form with said rim of said cap protector an annular channel in which is removably received and secured said channnular shaped intermediate member, said recess having an enlarged upper portion forming a pocket for removably receiving said cap, said cap having a top portion and a peripheral rim depending from said top portion, said rim of said cap being removably received and secured in the enlarged upper portion of said recess so that the inner surfaces of said cap form with the surfaces of said recess a closed chamber, said cap being of a size to fit over the opening and rim of said container after removal of said cap protector from said intermediate member and said intermediate member from said container and after said cap is removed from said pocket in said cap protector.

12. A device according to claim 11, said enlarged portion of said recess forming an annular shoulder in the wall of said recess, the edge of said rim of said cap lying over said shoulder, said rim of said container and said intermediate member lying under said shoulder and a portion of said recess below said shoulder depending into the opening in said intermediate member, the upper portion of said cap protruding from said pocket in said cap protector so that the outside thereof can be grasped by the hand and removed from said pocket.

13. A device according to claim 11, said cap, cap protector and intermediate member being color coded to facilitate compliance with use directions to reduce the risk of contamination during use and said cap protector and intermediate member each having a tab which can be grasped by the fingers of one hand for removal.

14. A specimen collecting device comprising a container having an open end for the collection of a specimen, said open end being formed by a rim of said container, an annular intermediate member of channular cross-sectional shape removably secured to, over and around the rim of the container, a cap protector removably secured to, over and around said annular member to close the opening of the annular member and thereby the container, and a cap removably secured to the top of said cap protector so that the internal surfaces of the cap are protected from contamination both when the cap protector is removed from said intermediate member and when it is secured thereto, said cap having a top portion and a peripherally depending side wall extending into a cap rim and being of a size to fit over and around said rim of said container to close said container, said cap protector having a portion extending over said opening of said intermediate member, said last mentioned portion being recessed into the opening of said intermediate member to form a pocket for removably receiving said rim of said cap so that the inner surfaces of said cap and of said pocket form a closed chamber, the upper part of said cap protruding out of said pocket so that the outside thereof can be grasped by the fingers to remove it from said pocket.

* * * * *